(12) United States Patent
Sakakibara et al.

(10) Patent No.: US 8,367,729 B2
(45) Date of Patent: Feb. 5, 2013

(54) COMPOSITION WITH PREVENTIVE OR IMPROVEMENT EFFECT ON SYMPTOMS OR DISEASES ASSOCIATED WITH STRESS-INDUCED BEHAVIOR DISORDERS

(75) Inventors: Manabu Sakakibara, Namazu (JP); Yoshiyuki Ishikura, Ibaraki (JP)

(73) Assignee: Suntory Holdings Limited, Osaka-shi, Osaka (JP)

( * ) Notice: Subject to any disclaimer, the term of this patent is extended or adjusted under 35 U.S.C. 154(b) by 0 days.

(21) Appl. No.: 13/465,546

(22) Filed: May 7, 2012

(65) Prior Publication Data

US 2012/0220660 A1 Aug. 30, 2012

Related U.S. Application Data

(62) Division of application No. 11/663,076, filed as application No. PCT/JP2005/005623 on Mar. 18, 2005.

(30) Foreign Application Priority Data

Sep. 17, 2004 (JP) ................................. 2004-271927

(51) Int. Cl.
*A61K 31/20* (2006.01)
(52) U.S. Cl. ...................................................... 514/560
(58) Field of Classification Search .................... 514/560
See application file for complete search history.

(56) References Cited

U.S. PATENT DOCUMENTS

| | | | |
|---|---|---|---|
| 4,526,902 A | 7/1985 | Rubin | |
| 4,668,704 A | 5/1987 | Hollander et al. | |
| 5,198,468 A | 3/1993 | Horrobin | |
| 5,583,019 A | 12/1996 | Barclay | |
| 5,866,703 A | 2/1999 | Horrobin et al. | |
| 5,902,807 A | 5/1999 | Haapalinna et al. | |
| 6,034,130 A | 3/2000 | Wang et al. | |
| 6,069,138 A | 5/2000 | Ponroy | |
| 6,080,787 A | 6/2000 | Carlson et al. | |
| 6,225,444 B1 | 5/2001 | Shashoua | |
| 2002/0040058 A1 | 4/2002 | Kiliaan et al. | |
| 2004/0219208 A1 | 11/2004 | Kawamura et al. | |
| 2004/0266874 A1 | 12/2004 | Akimoto et al. | |
| 2006/0057185 A1 | 3/2006 | Akimoto et al. | |
| 2006/0088573 A1 | 4/2006 | Ishikura et al. | |
| 2006/0217368 A1 | 9/2006 | Morishita et al. | |

FOREIGN PATENT DOCUMENTS

| | | |
|---|---|---|
| CA | 2109777 | 5/1994 |
| CA | 2596241 | 12/1994 |
| CA | 2 512 133 | 5/2005 |
| CN | 1155982 A | 8/1997 |
| CN | 1175976 | 3/1998 |
| CN | 1205839 | 1/1999 |
| EP | 0 234 733 B1 | 11/1991 |
| EP | 0 713 653 A1 | 5/1996 |
| EP | 09-023817 | 1/1997 |
| EP | 1 894 472 | 10/1997 |
| EP | 0 965 578 | 12/1999 |
| EP | 1 239 022 | 9/2002 |
| EP | 1 419 768 | 5/2004 |
| GB | 0111282.0 | 5/2001 |
| JP | 06256179 A | 9/1994 |
| JP | 8-143454 | 6/1996 |
| JP | 08214891 | 8/1996 |
| JP | 8-511533 | 12/1996 |
| JP | 09030962 | 2/1997 |
| JP | 10-101568 | 4/1998 |
| JP | 10-155459 | 6/1998 |
| JP | 10-191886 | 7/1998 |
| JP | 11034236 A | 2/1999 |
| JP | 2000-8074 | 1/2000 |
| JP | 2000-516261 | 12/2000 |
| JP | 2001-31586 A | 2/2001 |
| JP | 2003-48831 | 2/2003 |
| JP | 2003-504333 | 2/2003 |
| JP | 2003-113120 | 4/2003 |
| JP | 2006/076948 A | 3/2006 |
| JP | 2006-83134 | 3/2006 |
| JP | 2006-83136 | 3/2006 |
| JP | 2006-521369 | 9/2006 |
| JP | 2007-008863 | 1/2007 |
| WO | 94/28913 | 12/1994 |
| WO | WO 94/28891 | 12/1994 |
| WO | 96/10922 | 4/1996 |
| WO | 96/21037 | 7/1996 |
| WO | 98/50052 | 11/1998 |
| WO | 00/21524 | 4/2000 |
| WO | 01/03696 | 1/2001 |
| WO | WO-0124645 A1 | 4/2001 |
| WO | 01/85158 A2 | 11/2001 |
| WO | WO-0184961 A2 | 11/2001 |
| WO | 01/91745 A2 | 12/2001 |
| WO | 01/97793 A2 | 12/2001 |
| WO | 02/02105 | 1/2002 |
| WO | 02/19839 | 3/2002 |
| WO | 2002/089787 | 11/2002 |
| WO | 02/102394 A2 | 12/2002 |
| WO | 03/004667 | 1/2003 |

(Continued)

OTHER PUBLICATIONS

Lynch, "Analysis of the Mechanisms Underlying the Age-related Impairment in Long-Term Potentiation in the Rat," Reviews in the Neurosciences, vol. 9, pp. 169-201 (1998).

Crawford, "The role of essential fatty acids in neural development: implications for perinatal nutrition," Am. J. Clin. Nutr., pp. 703S-710S, vol. 57 (suppl) (1993).

Crawford at al., "Are deficits of arachidonic and docosahexaenoic acids responsible for the neural and vascular complications of preterm babies?," Am. J. Clin. Nutr., vol. 66 (suppl), pp. 1032S-1041S (1997).

(Continued)

*Primary Examiner* — Jennifer M Kim
(74) *Attorney, Agent, or Firm* — Drinker Biddle & Reath LLP

(57) ABSTRACT

A composition with a preventive or improvement effect on symptoms or diseases associated with stress-induced behavior disorders, comprising arachidonic acid and/or a compound comprising arachidonic acid as a constituent fatty acid.

22 Claims, 2 Drawing Sheets

FOREIGN PATENT DOCUMENTS

| WO | 03013497 A1 | 2/2003 |
|---|---|---|
| WO | 03/092673 A1 | 11/2003 |
| WO | 2004/024136 A1 | 3/2004 |
| WO | 2004/024930 A2 | 3/2004 |
| WO | 2004/028529 | 4/2004 |
| WO | 2004/084882 | 10/2004 |
| WO | 2004/091663 A1 | 10/2004 |
| WO | 2005/018632 | 3/2005 |
| WO | 2005/037848 A2 | 4/2005 |
| WO | 2005/072306 | 8/2005 |
| WO | 2006/030552 | 3/2006 |

OTHER PUBLICATIONS

Hempenius et al., "Preliminary Safety Assessment of an Arachidonic Acid-enriched Oil derived from *Mortierella alpina*: Summary of Toxicological Data," Food and Chemical Toxicology, vol. 35, pp. 573-581 (1997).

Birch et al., "A randomized controlled trial of early dietary supply of long-chain polyunsaturated fatty acids and mental development in term infants," Developmental Medicine & Child Neurology, vol. 42, pp. 174-181 (2000).

Kalmijn et al., "Dietary Fat Intake and the Risk of Incident Dementia in the Rotterdam Study," Annals of Neurology, pp. 776-782 (1997).

Soderberg et al., "Fatty Acid Composition of Brain Phospholipids in Aging and in Alzheimer's Disease," Lipids, vol. 26, No. 6, pp. 421-425 (1991).

Ferguson, Letter to Linda Kahl, Ph.D., Aug. 3, 2001, "Re: GRAS Notice for ARASCO® (arachidonic acid-rich single-cell oil) Level in Term Infant Formula."

Wieraszko, "Avian Hippocampus as a Model to Study Spatial Orientation-Related Synaptic Plasticity," Molecular and Cellular Mechanisms of Neuronal Plasticity, pp. 107-129 (1998).

Notice of Opposition against EP1419768 by Abbott Laboratories (May 17, 2012).

Notice of opposition against EP 1419768 by N.V. Nutricia (May 16, 2012).

Fields, Letter to Food and Drug Administration, Aug. 27, 1998, "Re: Notice of a claim for Exemption from Premarket Approval," available at htt://www.accessdate.fda.gov/scripts/fcn/gras_notices/grn_7.pdf. documents created in 1998.

Randolph, "Repeatable Battery for the Assessment of Neuropsychological Status (RBANSTM)," available at http://www.pearsonassessments.com/HAIWEB/Cultures/en-us/Productdetail.htm?Pid=015-8168-000 (last visited Jul. 3, 2012.

Anderson et al., "Breast-feeding and cognitive development: a meta-analysis," Am. J. Clin. Nutr., vol. 70, pp. 525-535, (1999).

D.A. Kharkevich, Farmakologiya [Pharmacology], M., Meditsina, 1987, pp. 41-42. (In Russian).

V.G. Belikov, Farmatsevticheskaya khimiya, [Pharmaceutical Chemistry], M., Vysshaya shkola, 1993, vol. 1, pp. 43-47. (In Russian).

Written Opinion mailed Nov. 7, 2006 in International PCT Application PCT/JP2006/313444 filed Jun. 29, 2006.

Office Action mailed Jan. 26, 2010 in Russian Application No. 2008103361/15(003664) with English language translation.

Search Report dated Nov. 7, 2006 for International Application No. PCT/JP2006/313444 filed Jun. 29, 2006.

Search Report dated Jul. 20, 2005 for International Patent Application No. PCT/JP2005/005622 filed Mar. 18, 2005.

Susumu Kotani et al., "Dietary supplementation of arachidonic and docosahexanoic acids improves cognitive dysfunction," 2006, pp. 159-164, vol. 56, Neuroscience Research, Limerick, Ireland.

Search Report dated Mar. 4, 2008 for International Application No. PCT/JP2007/075403 filed Dec. 27, 2007.

Yoshimura et al., "FGF-2 regulation of neurogenesis in adult hippocampus after brain injury," PNAS, May 8, 2001, vol. 98, No. 10, pp. 5874-5879.

Nakatomi et al., "Regeneration of Hippocampal Pyramidal Neurons after Ischemic Brain Injury by Recruitment of Endogenous Neural Progenitors," Cell, vol. 110, Aug. 23, 2002, pp. 429-441.

Kawakita et al., "Docosahexaenoic Acid Promotes Neurogenesis in Vitro and in Vivo," Neuroscience, 2006, vol. 139, pp. 991-997.

Hirano et al., "Influence of Taurine Load on Neural Development," Program of the 173$^{rd}$ Meeting of the Essential Amino Acid Research Council, 2003, p. 1 (with partial English-language translation).

European Search Report dated Jan. 27, 2010 in EP Application No. 07860598.7.

Search Report dated Jan. 31, 2007 for International Application No. PCT/JP2006/313437 filed Jun. 29, 2006.

Database WPI Week 200064, Derwent Publications Ltd., London, GB; AN 2000-658544, XP002410776.

Choi-Kwon, Smi et al., "Temporal changes in cerebral antioxidant enzyme activities after ischemia and reperfusion in a rat focal brain ischemia model: effect of dietary fish oil," Developmental Brain Research, Aug. 18, 2004, pp. 11-18, vol. 152, No. 1, XP007901417.

Supplementary European Search Report dated Aug. 30, 2010, issued in European patent application No. 04 79 3331.

Kark et al., "Adipose Tissue n-6 Fatty Acids and Acute Myocardial Infarction in a Population Consuming a Diet High in Polyunsaturated Fatty Acids", *Am J Clin Nutr*, 77, 796-802 (2003).

McNamara et al., "The Neuropharmacological and Neurochemical Basis of Place Learning in the Morris Water Water Maze," Brain Res. Rev., vol 18, pp. 33-49 (1993).

Reddy, "Preclinical and Clincal Behavioral Paradigms for Testing Drugs that Affect Learning and Memory Processes," Methods Find. Exp. Clin. Pharmacol. vol. 20, No. 3, pp. 249-277 (1998).

McGahon et al,, "Age-Related Changes in Synaptic Function Analysis of the Effect of Dietary Supplementation with ω-3 Fatty Acids," Neuroscience, vol. 94, No. 1, 1999, pp. 305-314.

Office Action dated Jun. 28, 2010 in European Patent Application 03 748 553.9.

Science Daily, "Brain Atrophy in Elderly Leads to Unintended Racism, Depression and Problem Gambling," Association for Psychological Sciences, 2007.

Yuksel et al., "Evaluation of mental retardation—Part 1: Etiologic classification of 4659 patients with mental retardation or multiple congenital abnormality and mental retardation," J. Pediatr. Neurosci, vol. 2, (2007), pp. 45-52.

Office Action dated Sep. 3, 2010 in Russian Patent Application No. 2008103361/15(003664) (with English translation).

Psychiatry edited by R. Sheider, Moscow, Praktika, 1998, pp. 280-282 and 287-289 (with English Translation).

The Merck Manual, Fifteenth Edition 1987, pp. 1421-1424.

Simopoulos, "Essential fatty acids in health and chronic disease," Am. J. Clin, Nutr, (1999), vol. 70, pp. 560S-569S.

Happe et al., "Time to give up on a single explanation for autism," Nature Neuroscience, vol. 9, No. 10, Oct. 2006, pp. 1218-1220.

Vericel et al., "The influence of low intake of *n*-3 fatty acids on platelets in elderly people," Atherosclerosis, vol. 147, (1999) pp. 187-192.

Nakawatase et al., "Alzheimer's Disease and Related Ementias," Cecil's Textbook of Medicine. (Twenty-First Edition, vol. 1), W.B. Saunders Company, 2000, pp. 2042-2045.

Hart et al, "The Contribution of Risk Factors to Stroke Differentials, by Socioeconomic Position in Adulthood. The Renfrew/Paisley Study," Am. J. of Public Health, vol. 90, No. 11 (Nov. 2000), pp. 1788-1791.

Vance [Editor], Biochemistry of Lipids and Membranes, 1985, pp. 330-331.

Belmonte et al., "Fragile X syndrome and autism at the intersection of genetic and neural networks," Nat. Neurosci., vol. 9, No. 10 (Oct. 2006), pp. 1221-1225.

Office Action dated Jun. 8, 2010 in Japanese Patent Application JP2004-539481 (in Japanese).

Kelley et al., "Arachidonic Acid Supplementation Enhances Synthesis of Eicosanoids Without Suppressing Immune Functions in Young Healthy Men," Lipids, vol. 33, No. 2 (1998) pp. 125-130.

Lynch et al., "Impaired Spatial Memory in Aged Rates is Associated with Alterations in Inositol Phospholipid Metabolism," NeuroReport, vol. 5, 1994, pp. 1493-1497, Lippincott Williams & Wilkins, London, England.

Wainwright et al., "Water Maze Performance is Unaffected in Artificially Reared Rats Fed Diets Supplemented with Arachidonic Acid and Docosahexaenoic Acid," J. Nutr., vol. 129, 1999, pp. 1079-1089. American Society for Nutritional Sciences, Bethesda, MD.

Wainwright et al., Arachidonic Acid Offsets the Effects on Mouse Brain and Behavior of a Diet with a Low (n-6):(n-3) Ratio and Very High Levels of Docosahaenoic Acid, J. Nutr., vol. 127, 1997, pp. 184-193, American Society for Nutritional Sciences, Bethesda, MD.

Youdim et al., "Essential Fatty Acids and the Brain: Possible Health Implications," Int. J. Dev. Neurosci., vol. 18, 2000, pp. 383-399, Oxford Elsevier Science, New York, NY (Abstract Only).

Kawashtma et al., "Enzymatic Synthesis of High-Purity Structured Lipids with Caprylic Acid at 1,3-Positions and Polyunsaturated Fatty Acid at 2-Position," J. Am. Oil Chem. Soc., vol. 78, 2001, pp. 611-616, American Oil Chemists Society, Champaign, IL.

MacKay & Mochly-Rosen, "Arachidonic Acid Protects Neonatal Rat Cardiac Myocytes from Ischaemic Injury though ε Protein Kinase C.," Cardiovascular Res. vol. 50, 2001, pp. 65-74, Elsevier Science B.V., Amsterdam, Holland.

Horrobin, "Abnormal Membrane Concentrations of 20 and 22-Carbon Essential Fatty Acids: A Common Link Between Risk Factors and Coronary and Peripheral Vascular Disease," Prostaglandins Leukot. Essent. Fatty Acids, vol. 53, 1995, pp. 385-396, Churchill Livingstone, Edinburgh, Scotland.

Webster's Third New International Dictionary, 1963, p. 1798, G.& C. Merriam Co., Springfield, MA.

Strub, "Vascular Dementia," South. Med. J., vol. 96, 2003, pp. 363-366, Southern Medical Association, Birmingham, AL.

McGahon et al., "The Ability of Aged Rats to Sustain Long-Term Potentiation is Restored when the Age-Related Decrease in Membrane Arachidonic Acid Concentration is Reversed", Neuroscience, vol. 81, (1997), pp. 9-16.

Koletzko et al., "Polyunsaturated fatty acids in human milk and their role in early infant development," Journal of Mammary Gland Biology and Neoplasia, Jul. 1999, pp. 269-294, vol. 4, No. 3.

Carlson S.E., "Docosahexaenoic acid and arachidonic acid in infant development," Seminars in Neonatology, Oct. 2001, pp. 437-449, vol. 6, No. 5.

Auestad et al., "Visual, cognitive, and language assessments at 39 months: a follow-up study of children fed formulas containing long-chain polyunsaturated fatty acids to 1 year of age," Pediatrics, Sep. 2003, pp. e177-e183, vol. 112, No. 3, Pt I.

Willatts et al., "Effect of Long-Chain Polyunsaturated Fatty Acids in Infant Formula on Problem Solving at 10 Months of Age," Lancet, vol. 352, 1998, pp. 688-691, Lancet, Publishing Group, London, England.

Lucas et al., "Efficacy and safety of long-chain polyunsaturated fatty acid supplementation of infant-formula milk: a randomized trial, " LANCET, Dec. 4, 1999, pp. 1948-1954, vol. 354 No. 9194.

Office Action dated Oct. 16, 2008 in Canadian Patent Application No. 2,456,049.

Office Action dated Mar. 2, 2010 in Japanese Patent Application No. 2004-539481 (In Japanese).

Kotani et al. "Improvement of Synaptic plasticity in the hippocampus of aged rats by ingestion of arachidonic acid," $24^{th}$ Japan Neurosurigical Society Program, (2001), p. 243. (In Japanese w/English translation.

Office Action issued Jan. 4, 2011, in Japanese Patent Application No. 2009-147715 (in Japanese).

Novel Food Information—DHASCO® and ARASCO® from Health Canada, Date Modified Jan. 31, 2003.

Song et al., "Effects of dietary n-3 or n-6 fatty acids on interleukin-1β-induced anxiety, stress, and inflammatory responses in rats," J. Lipid Res. Oct. 2003, vol. 44, No. 10, pp. 1984-1991 (electronically published Jul. 1, 2003).

Mills et al., "Psychosocial stress, catecholamines, and essential fatty acid metabolism in rats," Proc. Soc. Exp. Biol. Med. Jan. 1994, vol. 205, No. 1, pp. 56-61.

Office Action issued Feb. 17, 2011 in Chinese Patent Application No. 200480001751.X (with English translation).

Japanese Office Action dated Jul. 19, 2011 in JP 2005-191506 (in Japanese).

K. Naliwaiko et al., "Effects of Fish Oil on the Central Nervous System: A New Potential Antidepressant?" Nutritional Neuroscience, vol. 7, No. 2 (Apr. 2004), pp. 91-99.

Golfeito et al., Nutr. Neurosci., 2001, 4(1), 75-79, abstract.

Japanese Office Action dated Jul. 12, 2011 in JP 2004-271958 (in Japanese).

Yakkyoku (Pharmacy), 2000, vol. 51, No. 2, p. 2-10 (w/ partial English Translation).

Modern Physician, 2002, vol. 22, No. 9, p. 1155-1157 (w/ partial English translation).

Japanese Office Action dated Aug. 9, 2011 in JP 2005-191624 (in Japanese).

M. Minami et al., "Dietary Docosahexaenoic Acid Increases Cerebral Acetylcholine Levels and Improves Passive Avoidance performance in Stroke-Prone Spontaneously Hypertensive Rats" Pharmacology Biochemistry and Behavior, vol. 58, No. 4, pp. 1123-1129 (1997).

Russian Office Action dated Sep. 14, 2011 in Russian Application No. 2008103361/15(003664) (w/ English translation).

Bolshaya Rossijskaya Entsyclopediya, 1992, vol. 3, p. 202 (w/English translation).

Korean Office Action dated Sep. 27, 2011 in Korean patent application No. 7005102/2005 (w/ English translation).

Gordon, "Nutrition and cognitive function," Brain & Development 19 (1997) pp. 165-170.

Taiwanese Office Action issued Mar. 24, 2011 in Taiwanese Patent Application No. 092126198 (in Chinese).

European Office Action issued May 2, 2011 in European Patent Application No. 06780813.9.

Ulmann et al., "Brain and hippocampus fatty acid composition in phospholipid classes of aged-relative cognitive deficit rats," Prostaglandins, Leukotrienes and Essential Fatty Acids, vol. 64, Issue 3, Mar. 2001 (abstract).

The Merck Manual of Diagnosis and Therapy, 18th Ed., Merck Research Laboratories, 2006; pp. 1816-1818.

Office Action dated Jan. 18 2011 issued in Japanese Patent Application. No. 2004-271927 (In Japanese).

Kawashima et al., "Enzymatic Synthesis of High-Purity Structured Lipids with Caprylic Acid at 1,3-Positions and Polyunsaturated Fatty Acid at 2-Position," JAOCS, vol. 78, No. 6 (2001).

Office Action dated Jan. 11, 2011 issued in Japanese Patent Application No. 2001-235519 (In Japanese).

Wollan et al., "Dietary essential fatty acids gender-specific difference in rat maze learning and memory," Neuroscience Abstract, 2000, No. 793.13, Society for Neuroscience, vol. 26.

John R. Burgess et al.; "Long-Chain Polyunsaturated Fatty Acids In Children with Attention-Deficit Hyperactivity Disorder", American Journal of Clinical Nutrition, Bethesds, MD, US, vol. 71, No. 1, Suppl, Jan. 2000, pp. 237S-330S; XP008000462.

Louis-Joseph Auguste, M.D., et al.; "Prevention of Stress-Induced Erosive Gastritis by Parenteral Administration of Arachidonic Acid"; Journal of Parenteral and Enteral Nutrition; vol. 14, No. 6, 1990, pp. 615-617; XP009049858.

Search Report dated Jul. 11, 2005 from International PCT Application No. PCT/JP2005/005623.

Office Action dated Sep. 22, 2011 issued in Australian Patent Application No. 2005283697.

Stevens et al., "EFA Supplementation in Children with Inattention, Hyperactivity, and Other Disruptive Behaviors," Lipids, vol. 38, No. 10, (2003), pp. 1007-1021.

Gorelick et al., "Stroke Prevention Therapy Beyond Antithrombotics: Unifying Mechanisms in Ischemic Stroke Pathogenesis and Implications for Therapy: An Invited Review," Stroke, vol. 33, pp. 862-875 (2002).

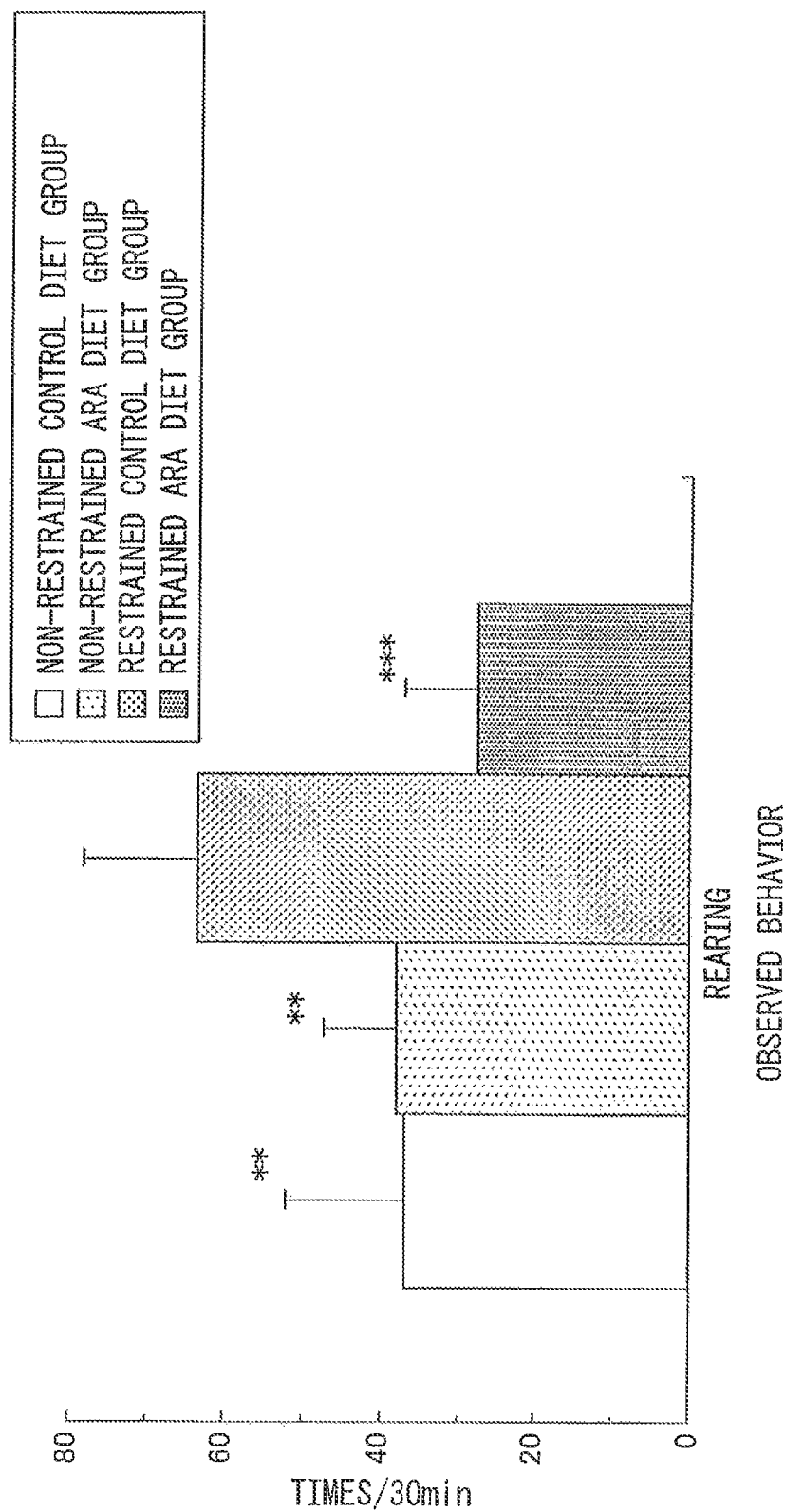

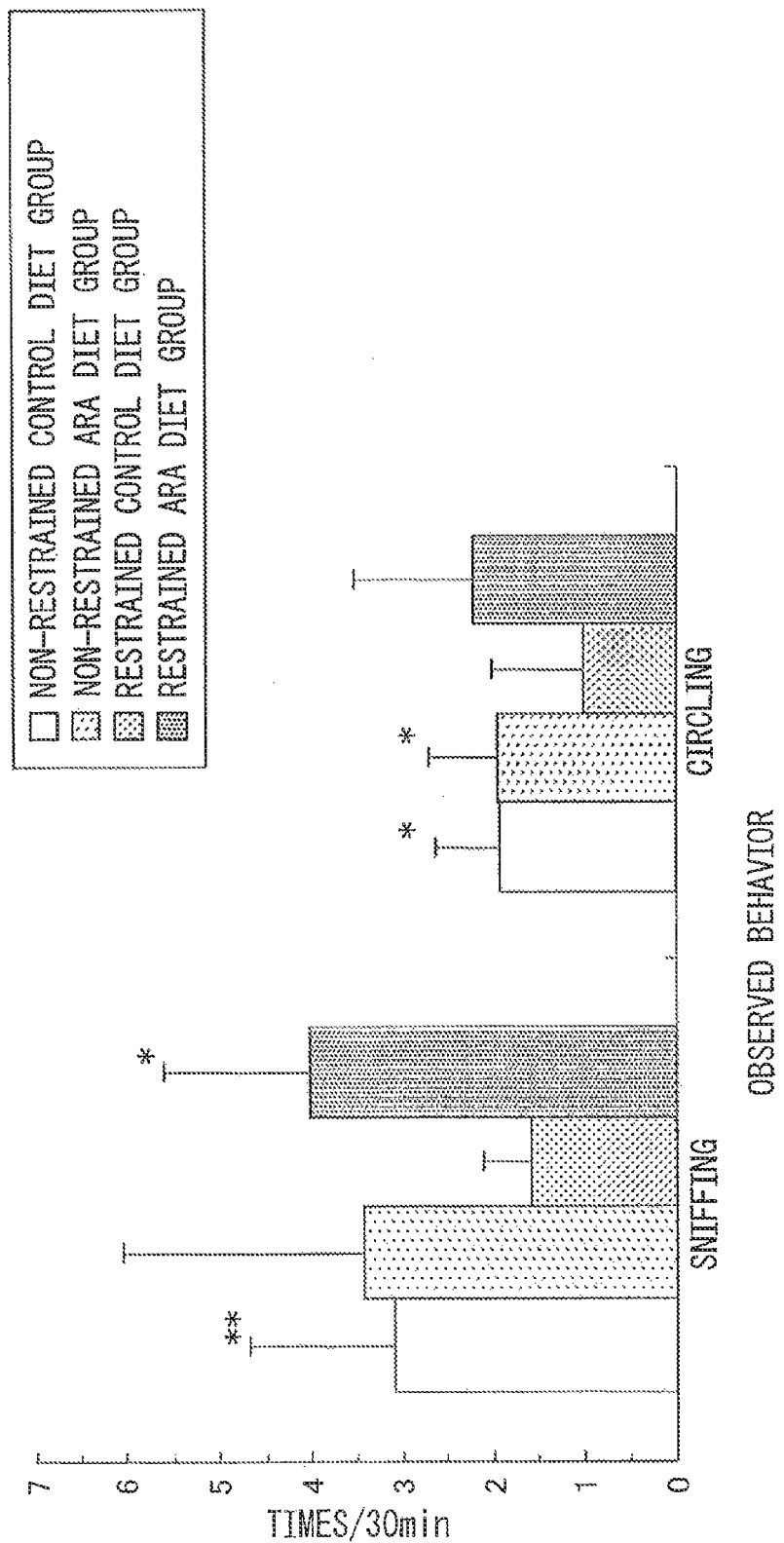

COMPOSITION WITH PREVENTIVE OR IMPROVEMENT EFFECT ON SYMPTOMS OR DISEASES ASSOCIATED WITH STRESS-INDUCED BEHAVIOR DISORDERS

CROSS REFERENCE TO RELATED APPLICATIONS

This application is a divisional of U.S. Application No. 11/663,076 filed Mar. 16, 2007, which is the National Stage of International Application No, PCT/P2005/005623 filed Mar. 18, 2005, which claims benefit of Japanese Patent Application No. 2004-271927, filed on Sep. 17, 2004, and which are incorporated by reference herein in their entirety.

TECHNICAL FIELD OF THE INVENTION

The present invention relates to a preventive or improvement agent for symptoms or diseases associated with stress-induced behavior disorders, comprising as an active ingredient arachidonic acid and/or a compound comprising arachidonic acid as a constituent fatty acid, as well as to a composition with a preventive or improvement effect on symptoms or diseases associated with stress-induced behavior disorders, and a method for its production. More specifically, the invention relates to a preventive or improvement agent for stress-induced habits such as finger sucking and onychophagy, adjustment disorder, attention deficit hyperactivity disorder, acute stress disorder or posttraumatic stress disorder, comprising as an active ingredient at least one selected from the group consisting of arachidonic arachidonic acid alcohol esters, and triglycerides, phospholipids or glycolipids wherein all or a portion of the constituent fatty acid is arachidonic acid, as well as to a food or beverage with such a preventive or improvement effect and a method for its production.

BACKGROUND ART

Stress is recognized as a response which can lead to behavior disorders, and the symptoms associated with stress-induced behavior disorders are known as stress-related disorders; these are classified into several types of symptoms based on two factors: the nature of the stress and the disposition of the individual experiencing the stress. The symptoms span a wide range from simple habits such as finger sucking or onychophagy seen primarily during the infant period and resulting from light stress factors, to adjustment disorder and attention deficit hyperactivity disorder which are considered to be highly influenced by individual disposition, and further to acute stress disorder or posttraumatic stress disorder, which are associated with extremely intense stress beyond individual disposition (Shindan to Chiryo 91, 1333, 2003).

Recently, increased blood IL-1β has been reported in posttraumatic stress disorder patients (Biol. Psychiatry 42, 345, 1997), and research has focused on the relationship between IL-1β and neuronopathy.

Drugs used for stress-related disorders include benzodiazepine-based drugs used for insomnia and anxiety, serotonin reuptake inhibitors and tricyclic antidepressant drugs used to alleviate symptoms flashbacks, adrenaline antagonists and anticonvulsant drugs used for symptoms of hypervigilance, and antipsychotic agents used for exaggerated startle response or increased irritability. However, all such agents are symptomatic treatment for improvement of superficial symptoms such as depression, insomnia and excitement, and unfortunately no agents for causal treatment exist at this time.

One possible treatment for stress-related disorders is to suppress their progression by removing the cause of stress. However, given the modern environment it is very difficult to eliminate the causative factors of stress.

Thus, to date no drug has existed which is effective as a pharmaceutical agent having a preventive or improvement effect on symptoms or diseases associated with stress-induced behavior disorders. Furthermore, applications to food products have been hampered by the limitation to components which produce no side effects.

The brain consists of a lipid mass-like tissue, with phospholipids constituting about ⅓ of the white matter and about ¼ of the gray matter. The polyunsaturated fatty acids in phospholipids of the various cell membranes in the brain consist primarily of arachidonic acid and docosahexaenoic acid. However, arachidonic acid and docosahexaenoic acid (DHA) cannot be synthesized de novo in animal bodies and must be directly or indirectly obtained through diet (for example, as the arachidonic acid and docosahexaenoic acid precursors, linoleic acid and α-linolenic acid).

Burgess et al. have demonstrated that arachidonic acid and DHA contents of plasma phospholipids are significantly lower in posttraumatic stress disorder patients (Am J Clin Nutr 71, 327S, 2000). It has also been reported that liver microsome Δ5-desaturase and Δ6-desaturase activity is reduced in separately bred stress model rats (Proc Soc Exp Biol Med. 205, 56, 1994), and the reduction in activity of these desaturases is believed to be responsible for a lack of brain levels of arachidonic acid and DHA, polyunsaturated fatty acids with a high degree of unsaturation.

On the other hand, several experiments have been reported using administration of arachidonic acid to animal stress models. Song et al. reported that administration of free arachidonic acid was not effective for IL-1β induced stress anxiety behavior models (J Lipid Res. 44, 1984, 2003). Also, Clements et al. describe giving attention deficit hyperactivity disorder (ADHD) models (spontaneously hypertensive rats, SHR) feed containing 0.5% arachidonic acid and 0.9% DHA for 8 weeks, and reported increased DHA in the brain phospholipids but no observable effect (Dev Psychobiol. 43, 57, 2003). No other reports indicate that administration of arachidonic acid improves stress-induced behavior disorders.

Thus, while it has been reported that arachidonic acid levels in the body are lowered by stress, it has not been clearly demonstrated whether arachidonic acid or compounds including arachidonic acid as a constituent fatty acid according to the invention are effective for the prevention or improvement of symptoms or diseases associated with stress-induced behavior disorders, and in fact the experiments conducted to date have been definitively negative.

Non-patent document 1: Shindan to Chiryo 91, 1333, 2003
Non-patent document 2: Biol. Psychiatry 42, 345, 1997
Non-patent document 3: Am J Olin Nutr 71, 327S, 2000
Non-patent document 4: Proc Soc Exp Biol Med. 205, 56, 1994
Non-patent document 5: J Lipid Res. 44, 1984, 2003
Non-patent document 6: Dev Psychobiol. 43, 57, 2003

DISCLOSURE OF THE INVENTION

Thus, a strong demand exists for development of pharmaceuticals which prevent and improve symptoms or diseases associated with stress-induced behavior disorders, as well as such compounds which are highly suitable for consumption and lacking notable side effects.

As a result of much diligent research conducted with the purpose of elucidating the preventive or improvement effects on symptoms or diseases associated with stress-induced behavior disorders by agents comprising as active ingredients arachidonic acid and/or compounds comprising arachidonic acid as a constituent fatty acid, the present inventors found that the active ingredients of the invention exhibit apparent behavioral pharmacologic effects in a behavioral observation test using mice subjected to restraint stress, which is considered to approximate human emotional stress.

We also succeeded in realizing industrial production of a triglyceride containing at least 10% microbially generated arachidonic acid, and supplied the triglyceride for testing in order to elucidate the effect of the invention.

Specifically, the present invention provides a preventive or improvement agent for symptoms or diseases associated with stress-induced behavior disorders and a composition with a preventive or improvement effect on symptoms or diseases associated with stress-induced behavior disorders, comprising as an active ingredient arachidonic acid and/or a compound comprising arachidonic acid as a constituent fatty acid, as well as a method for their production. More specifically, the invention provides a preventive or improvement agent for stress-induced habits such as finger sucking and fingernail biting, adjustment disorder, attention deficit hyperactivity disorder, acute stress disorder or posttraumatic stress disorder, comprising as an active ingredient at least one selected from the group consisting of arachidonic acid, arachidonic acid alcohol esters, and triglycerides, phospholipids or glycolipids wherein all or a portion of the constituent fatty acid is arachidonic acid, as well as to a composition with such a preventive or improvement effect and a method for its production.

BRIEF DESCRIPTION OF THE DRAWINGS

FIG. 1 is a graph showing the results for Example 3, indicating the effect of arachidonic acid on the rearing behavior of stressed mice.

FIG. 2 is a graph showing the results for Example 3, indicating the effect of arachidonic acid on the ultromotivity of stressed mice.

BEST MODE FOR CARRYING OUT THE INVENTION

The present invention relates to a preventive or improvement agent for symptoms or diseases associated with stress-induced behavior disorders and a composition with a preventive or improvement effect on symptoms or diseases associated with stress-induced behavior disorders, comprising as an active ingredient arachidonic acid and/or a compound comprising arachidonic acid as a constituent fatty acid, as well as a method for their production.

As "symptoms or diseases associated with stress-induced behavior disorders" there may be mentioned habits such as finger sucking and onychophagy, adjustment disorder, attention deficit hyperactivity disorder, acute stress disorder or posttraumatic stress disorder, but the symptoms and diseases are not limited to these and include all symptoms and diseases associated with stress-induced behavior disorders.

The active ingredient of the invention is arachidonic acid, but any compound comprising arachidonic acid as a constituent fatty acid may be used. As compounds comprising arachidonic acid as a constituent fatty acid there may be mentioned arachidonic acid salts, such as calcium or sodium salts. There may also be mentioned arachidonic acid lower alcohol esters such as arachidonic acid methyl ester and arachidonic acid ethyl ester. There may also be used triglycerides, phospholipids or glycolipids wherein all or a portion of the constituent fatty acid is arachidonic acid. However, the invention is not limited to the compounds mentioned above, and includes any compound comprising arachidonic acid as a constituent fatty acid.

For application to food products, the arachidonic acid is preferably in the form of a triglyceride or phospholipid, and most preferably in the form of a triglyceride. While virtually no natural sources of arachidonic acid-containing triglycerides (i.e., triglycerides including a triglyceride wherein all or a portion of the constituent fatty acid is arachidonic acid) exist, the present inventors have been the first to clearly demonstrate that it is possible to industrially utilize triglycerides comprising arachidonic acid as a constituent fatty acid, that the active ingredients of the invention exhibit apparent behavioral pharmacologic effects in mice subjected to restraint stress and evaluated by a behavioral observation test and have preventive or improvement effects for symptoms or diseases associated with stress-induced behavior disorders, and that the effects are attributable to arachidonic acid.

According to the invention, therefore, triglycerides including a triglyceride wherein all or a portion of the constituent fatty acid is arachidonic acid (arachidonic acid-containing triglycerides) may be used as the active ingredients of the invention. For application in foods, the arachidonic acid-containing triglycerides are preferably oils or fats (triglycerides) in a form wherein the arachidonic acid content of the total constituent fatty acid of the triglycerides is at least 10 wt % (w/w), more preferably at least 20 wt %, even more preferably at least 30 wt %, and most preferably at least 40 wt %. Thus, the present invention may employ any such compounds which are obtained by culturing microorganisms capable of producing arachidonic acid-containing oils or fats (triglycerides).

As microorganisms capable of producing oils or fats (triglycerides) containing arachidonic acid; there may be mentioned microorganisms belonging to the genera *Mortierella, Conidiobolus, Pythium, Phytophthora, Penicillium, Cladoporium, Mucor, Fusarium, Aspergillus, Rhodotorula, Entornophthora, Echinosporangium* and *Sapro egnia*.

As examples of microorganisms belonging to the genus *Mortierella*, subgenus *Mortierella*, there may be mentioned *Mortierella elongate, Mortierella exigua, Mortierella hygrophila* and *Mortierella alpina*. More specifically, there may be mentioned the strains *Mortierella elongate* IFO8570, *Mortierella exigua* IFO8571, *Mortierella hygrophila* IFO5941, and *Mortierella alpine* IFO8568, ATCC16266, ATCC32221, ATCC42430, CBS219.35, CBS224.37, CBS250.53, CBS343.66, CBS527.72, CBS529.72, CBS608.70, CBS754.68, etc.

All of these strains may be acquired without any special restrictions from the Institute for Fermentation, Osaka (IFO), American Type Culture Collection (ATCC) or Centralbureau voor Schimmelcultures (CBS). There may also be used the strain *Mortierella elongata* SAM0219 (FERM-P 8703) (deposited under the provisions of the Budapest Treaty on Mar. 19, 1986 with the Patent Microorganism Depository of National Institute of Industrial Science and Technology at Chuo 6, 1-1, Higashi 1-chome, Tsukuba city, Ibaraki pref., Japan, as FERM BP-1239), isolated from soil by the research group for the present invention.

For culturing of a strain to be used for the invention, spores, hypha or a pre-culture solution obtained by pre-culturing the strain may be seeded in a liquid medium or solid medium for culturing. In the case of liquid culturing, the carbon source used may be a common one such as glucose, fructose, xylose, saccharose, maltose, soluble starch, molasses, glycerol or mannitol, although there is no limitation to these.

As nitrogen sources there may be used organic nitrogen sources including urea, and natural nitrogen sources such as peptone, yeast extract, malt extract, meat extract, casamino acid, corn, steep liquor, soybean protein, defatted soybean and cotton seed meal, or inorganic nitrogen sources such as sodium nitrate, ammonium nitrate and ammonium sulfate. Trace nutrient sources including inorganic salts such as phosphoric acid salts, magnesium sulfate, iron sulfate and copper sulfate, or vitamins, may also be used if necessary. The medium components are not particularly restricted so long as they are in concentrations which do not prevent growth of the microorganisms. For most practical applications the carbon source may be used at a concentration of 0.1-40 wt % and preferably 1-25 wt %. The initial nitrogen source addition may be at 0.1-10 wt % and preferably 0.1-6 wt %, with further feeding of the nitrogen source during culturing.

By controlling the carbon source concentration of the medium it is possible to obtain oils or fats (triglyceride) containing at least 45 wt % arachidonic acid as the active ingredient of the invention. The cell growth phase is the culturing period up to the 2nd-4th day of culturing, while the fat/oil accumulation phase is from the 2nd-4th day of culturing. The initial carbon source concentration is 1-8 wt % and preferably 1-4 wt %, with successive supplemental addition of the carbon source only between the cell growth phase and the early fat/oil accumulation phase, for a total supplemental carbon source addition of 2-20 wt % and preferably 5-15 wt %. The amount of carbon source added between the cell growth phase and the early fat/oil accumulation phase will depend on the initial nitrogen source concentration, and if the carbon source concentration in the medium is 0 from the 7th day of culturing, preferably from the 6th day of culturing and more preferably from the 4th day of culturing, it will be possible to obtain oils or fats (triglyceride) containing at least 45 wt % arachidonic acid, as the active ingredient of the invention.

The culturing temperature for the arachidonic acid-producing cells will differ depending on the microorganism used, but is 5-40° C., preferably 20-30° C., while culturing at 20-30° C. for proliferation of the cells may also be followed by continued culturing at 5-20° C. to produce unsaturated fatty acids. Such temperature control can also be utilized to increase the proportion of polyunsaturated fatty acids among the produced fatty acids. The pH of the medium may be 47-10 and preferably 5-9, for jar fermentor culturing, shake culturing or stationary culturing. The culturing is normally carried out for 2-30 days, preferably 5-20 days and more preferably 5-15 days.

In addition to controlling the carbon source concentration of the medium as a strategy for increasing the proportion of arachidonic acid in the arachidonic acid-containing oils or fats (triglyceride), arachidonic acid-rich oils or fats may also be obtained by selective hydrolysis of the arachidonic acid-containing oils or fats. Since lipases used for such selective hydrolysis do not have regiospecificity for triglycerides and the hydrolytic activity decreases in proportion to the number of double bonds, the ester bonds of the fatty acids other than the polyunsaturated fatty acids are preferentially hydrolyzed. Furthermore, ester-exchange reaction between the produced PUFA glycerides may be used to produce triglycerides with an increased polyunsaturated fatty acid content ("Enhancement of Arachidonic Acid: Selective Hydrolysis of a Single-Cell Oil from *Mortierella* with *Candida cylindracea* Lipase": J. Am. Oil Chem. Soc., 72, 1323-1327, 1998).

Thus, oils or fats (triglyceride) with a high content of arachidonic acid obtained by selective hydrolysis of arachidonic acid-containing oils or fats can be prepared as the active ingredient of the invention. The proportion of arachidonic acid with respect to the total fatty acid content of the arachidonic acid-containing oils or fats (triglyceride) of the invention is preferably higher from the standpoint of eliminating the effect of other fatty acids, but it does not necessarily have to be a high proportion, and in fact the absolute amount of arachidonic acid can pose a problem for application to some foods. Oils or fats (triglycerides) containing arachidonic acid at 10 wt % or greater can be suitably used in most cases.

As triglycerides wherein all or a portion of the constituent fatty acid is arachidonic acid according to the invention, there may be used triglycerides having medium chain fatty acids bonded at the 1,3-positions and arachidonic acid bonded at the 2-position. The oils or fats (triglycerides) used may also comprise at least 5 mole percent, preferably at least 10 mole percent, more preferably at least 20 mole percent and most preferably at least 30 mole percent, of triglycerides having medium chain fatty acids bonded at the 1,3-positions and arachidonic acid bonded at the 2-position. The medium chain fatty acids bonded at the 1,3-positions of the triglyceride may be selected from among C6-12 fatty acids. As examples of C6-12 fatty acids there may be mentioned caprylic acid or capric acid, with 1,3-capryloyl-2-arachidonoyl-glycerol (hereinafter, "8A8") being particularly preferred.

Such triglycerides having medium chain fatty acids bonded at the 1,3-positions and arachidonic acid bonded at the 2-position are optimum oils or fats (triglycerides) for elderly persons. Generally speaking, ingested oils or fats (triglycerides) are hydrolyzed by pancreatic lipases upon entering the small intestine, but since pancreatic lipases are 1,3-specific, the 1,3-positions of the triglycerides are cleaved to form two free fatty acids while simultaneously producing a single 2-monoacylglycerol (MG). As 2-MG has extremely high bile solubility and is highly absorbable, the 2-position fatty acid is generally considered to be better absorbed. In addition, 2-MG dissolved in bile acid acts as a surfactant and thus increases the absorption of the free fatty acids.

The free fatty acids and 2-MG then form bile acid complex micelles together with cholesterol, phospholipids and the like and are incorporated into the intestinal epithelial cells where triacylglycerols are resynthesized, being finally released into the lymph as chylomicrons. However, the fatty acid specificity of pancreatic lipases is higher for saturated fatty acids, whereas arachidonic acid is not as easily cleaved. Another problem is that pancreatic lipase activity declines with age, and therefore triglycerides having medium chain fatty acids bonded at the 1,3-positions and arachidonic acid bonded at the 2-position are more optimal oils or fats (triglycerides) for the elderly.

One specific production method for triglycerides having medium chain fatty acids bonded at the 1,3-positions and arachidonic acid bonded at the 2-position is a method using a lipase which acts only on the 1,3-position ester bonds of triglycerides, in the presence of arachidonic acid-containing oils or fats (triglyceride) and a medium chain fatty acid.

The oils or fats (triglyceride) starting material are a triglyceride comprising arachidonic acid as a constituent fatty acid, but in the case of a high proportion of arachidonic acid with respect to the total constituent fatty acid of the triglycerides, reduced reaction yield due to excess unreacted oils or fats (the triglyceride starting material and triglycerides wherein only one of the 1,3-position-fatty acids has been converted to a medium chain fatty acid) can be prevented if the temperature is above the normal enzyme reaction temperature of 20-30° C., such as 30-50° C. and preferably 40-50° C.

As examples of lipases which act specifically on the 1,3-position ester bonds of triglycerides there may be mentioned lipases produced by microorganisms such as *Rhizopus, Rhizomucor* and *Aspergillus*, as well as porcine pancreatic lipases. Any such commercially available lipases may be used. For example, there may be mentioned *Rhizopus delemar* lipase (Talipase, Tanabe Pharmaceutical Co., Ltd.), *Rhizomucor miehei* lipase (Ribozyme IM, Novo Nordisk Co., Ltd.) and *Aspergillus niger* lipase (Lipase A, Amano Pharmaceutical Co., Ltd.), although there is no limitation to these enzymes and any 1,3-specific lipases may be used.

The form of the lipase used is preferably an immobilized form on an immobilizing support in order to impart heat resistance to the enzyme, since the reaction temperature is 30° C. or above and preferably 40° C. or above for increased reaction efficiency. The immobilizing support may be a porous (highly porous) resin, for example, an ion-exchange resin with pores of approximately 100 Å or greater such as Dowex MARATHON WBA. However, this condition is not restrictive on the immobilizing support, and any immobilizing support capable of imparting heat resistance may be used.

The immobilizing support may be suspended in an aqueous solution of a 1,3-specific lipase at a weight proportion of 0.5-20 of the latter with respect to the former, and a 2- to 5-fold amount of cold acetone (for example, −80° C.) may be slowly added to the suspension while stirring to form a precipitate. The precipitate may then be dried under reduced pressure to prepare the immobilized enzyme. As a simpler method, a 1,3-specific lipase in a proportion of 0.05-0.4 with respect to the immobilizing support may be dissolved in a minimal amount of water and mixed with the immobilizing support while stirring and dried under reduced pressure to prepare the immobilized enzyme. This procedure can immobilize approximately 90% lipase on the support, but since absolutely no ester exchange activity will be exhibited in that state, pretreatment may be carried out in a substrate containing 1-10 wt % (w/v) water and preferably a substrate containing 1-3 wt % water, in order to activate the immobilized enzyme to maximum efficiency before it is provided for production.

The amount of water added to the reaction system is extremely important depending on the type of enzyme, because a lack of water will impede ester exchange while an excess of water will cause hydrolysis and a reduced glyceride yield (since hydrolysis will produce diglycerides and monoglycerides). However, if the immobilized enzyme used has been activated by pretreatment the amount of water added to the reaction system is no longer crucial, and an efficient ester exchange reaction can be carried out even in a completely water-free system. Also, selection of the type of enzyme agent may allow the pretreatment step to be omitted.

Thus, by using a heat-resistant immobilized enzyme and raising the enzyme reaction temperature, it is possible to efficiently produce triglycerides having medium chain fatty acids bonded at the 1,3-positions and arachidonic acid bonded at the 2-position (8A8), without lowering the reaction efficiency even for arachidonic acid-containing oils or fats (triglycerides) with low reactivity for 1,3-specific lipases.

A method for production of a dietary product having a preventive or improvement effect on symptoms or diseases associated with stress-induced behavior disorders, involves adding arachidonic acid and/or a compound including arachidonic acid as a constituent fatty acid alone, or in combination with a dietary material containing substantially no arachidonic acid or only a slight amount thereof. Here, a "slight amount" means that even if arachidonic acid is present in the dietary product material and a food composition containing it is ingested by a human, the amount does not reach the daily amount of arachidonic acid consumption according to the invention, as described hereunder.

An unlimited number of uses exist for oils or fats (triglycerides) wherein all or a portion of the constituent fatty acid is arachidonic acid: for example, they may be used as starting materials and additives for foods, beverages, cosmetics and pharmaceuticals. The purposes of use and amounts of use are also completely unrestricted.

As examples of food compositions there may be mentioned ordinary foods, as well as functional foods, nutritional supplements, food for specified health uses, preterm infant formula, term infant formula, infant foods, maternal foods or geriatric foods. As examples of fat/oil-containing foods there may be mentioned natural fat/oil-containing foods such as meat, fish and nuts, foods to which oils or fats are added during preparation, such as soups, foods employing oils or fats as heating media, such as donuts, oils or fats foods such as butter, processed foods to which oils or fats are added during processing, such as cookies, or foods which are sprayed or coated with oils or fats upon finishing, such as hard biscuits. Such compositions may also be added to agricultural foods, fermented foods, livestock feeds, marine foods and beverages which contain no oils or fats. They may also be in the form of functional foods or pharmaceuticals, and for example, in processed form such as enteral nutrients, powders, granules, lozenges, oral solutions, suspensions, emulsions, syrups and the like.

A composition of the invention may also contain various carriers or additives ordinarily used in foods and beverages, pharmaceuticals or quasi drugs, in addition to the active ingredient of the invention. Antioxidants are particularly preferred as additives to prevent oxidation of the active ingredient of the invention. As examples of antioxidants there may be mentioned natural antioxidants such as tocopherols, flavone derivatives, phyllodulcins, kojic acid, gallic acid derivatives, catechins, fukiic acid, gossypol, pyrazine derivatives, sesamol, guaiaol, guaiac acid, p-coumaric acid, nordihydroguaiaretic acid, sterols, terpenes, nucleotide bases, carotenoids, lignans and the like, and synthetic antioxidants including ascorbic palmitic acid esters, ascorbic stearic acid esters, butylhydroxyanisole (BHA), butylhydroxytoluene (BHT), mono-t-butylhydroquinone (TBHQ) and 4-hydroxymethyl-2,6-di-t-butylphenol (HMBP).

As tocopherols there may be mentioned $\alpha$-tocopherol, $\beta$-tocopherol, $\gamma$-tocopherol, $\delta$-tocopherol, $\epsilon$-tocopherol, $\zeta$-tocopherol, $\eta$-tocopherol and tocopherol esters (tocopherol acetate and the like), as well as tocopherol analogs. As examples of carotenoids there may be mentioned $\beta$-carotene, cantaxanthine, astaxanthine and the like.

The composition of the invention may also contain, in addition to the active ingredient of the invention, supports such as carrier supports, extenders, diluents, bulking agents, dispersing agents, excipients, binder solvents (for example, water, ethanol and vegetable oils), dissolving aids, buffering agents, dissolving accelerators, gelling agents, suspending agents, wheat flour, rice flour, starch, corn starch, polysaccharides, milk protein, collagen, rice oil, lecithin and the like. As examples of additives there may be mentioned vitamins, sweeteners, organic acids, coloring agents, aromatic agents, moisture-preventing agents, fibers, electrolytes, minerals, nutrients, antioxidants, preservatives, fragrances, humectants, natural food extracts, vegetable extracts and the like, although there is no limitation to these.

Arachidonic acid is the main active ingredient of the compound which is either arachidonic acid or comprises arachidonic acid as a constituent fatty acid. The daily intake of arachidonic acid from dietary sources has been reported to be 0.14 g in the Kanto region and 0.19-0.20 g in the Kansai region of Japan (Shishitsu Eiyougaku 4, 73, 1995), and in consideration of reduced oils or fats intake and reduced pancreatic lipase function in the elderly, a correspondingly greater amount of arachidonic acid must be ingested. Thus, the daily intake of the arachidonic acid or the compound comprising arachidonic acid as a constituent fatty acid according to the invention for an adult (for example, 60 kg body weight) is 0.001-20 g, preferably 0.01-10 g, more preferably 0.05-5 g and most preferably 0.1-2 g, based on the arachidonic acid content.

When the active ingredient of the invention is to be actually applied for a food or beverage product, the absolute amount of arachidonic acid in the product is an important factor. However, since the absolute amount added to foods and beverages will differ depending on the amount of consumption of those foods or beverages, triglycerides including a triglyceride wherein all or a portion of the constituent fatty acid is arachidonic acid may be added to food products in amounts of at least 0.001 wt %, preferably at least 0.01 wt % and more preferably at least 0.1 wt % in terms of arachidonic acid. For addition to food and beverage products of triglycerides having medium chain fatty acids bonded at the 1,3-positions and arachidonic acid bonded at the 2-position, the amount may be at least 0.0003 wt %, preferably at least 0.003 wt % and more preferably at least 0.03 wt %.

When the composition of the invention is to be used as a pharmaceutical, it may be produced according to a common method in the field of pharmaceutical preparation techniques, such as according to a method described in the Japanese Pharmacopeia or a similar method.

When the composition of the invention is to be used as a pharmaceutical, the content of the active ingredient in the composition is not particularly restricted so long as the object of the invention is achieved, and any appropriate content may be employed.

When the composition of the invention is to be used as a pharmaceutical, it is preferably administered in the form of an administrable unit, and especially in oral form. The dosage of the composition of the invention will differ depending on age, body weight, symptoms and frequency of administration, but for example, the arachidonic acid and/or compound including arachidonic acid as a constituent fatty acid according to the invention may be administered at about 0.001-20 g, preferably 0.01-10 g, more preferably 0.05-5 g and most preferably 0.1-2 g (as arachidonic acid) per day for adults (approximately 60 kg), either once a day or divided among multiple doses, such as three separate doses.

The major fatty acid components of phospholipid membranes in the brain are arachidonic acid and docosahexaenoic acid, and therefore from the standpoint of balance, a combination with docosahexaenoic acid is preferred. Also, since the proportion of eicosapentaenoic acid in brain phospholipid membranes is very small, a combination of arachidonic acid and docosahexaenoic acid containing virtually no eicosapentaenoic acid is especially preferred. Furthermore, the arachidonic acid/docosahexaenoic acid ratio in the combination of the arachidonic acid and docosahexaenoic acid is preferably in the range of 0.1-15, and more preferably in the range of 0.25-10. Also, the amount of eicosapentaenoic acid in the food or beverage preferably does not exceed ⅕ of the arachidonic acid (weight ratio).

EXAMPLES

The present invention will now be explained in greater detail by the following examples, with the understanding that the invention is not limited to these examples.

Example 1 Method for Production of Arachidonic Acid-Containing Triglycerides

*Mortierella alpina* CBS754.68 was used as the arachidonic acid-producing strain. After preparing 6 kL of medium containing 1.8% glucose, 3.1% defatted soybean powder, 0.1% soybean oil, 0.3% $KH_2PO_4$, 0.1% $Na_2SO_4$, 0.05% $CaCl_2 \cdot 2H_2O$ and 0.05% $MgCl_2 \cdot 6H_2O$ in a 10 kL culturing tank, the initial pH was adjusted to 6.0.

A 30 L portion of the preculturing solution was transferred for 8 days of jar fermentor culturing under conditions with a temperature of 26° C., an airflow of 360 $m^3$/h and an internal pressure of 200 kPa. The stirring rate was adjusted to maintain a dissolved oxygen concentration of 10-15 ppm. Also, the glucose concentration was adjusted by the feeding culture method for a glucose concentration in the range of 1-2.5% in the medium up to the 4th day, with 0.5-1% maintained thereafter (where the percentage values are weight (W/V)%).

After completion of the culturing, the cells containing triglycerides having arachidonic acid as constituent fatty acid were collected by filtration and drying, and the fat and oil portion was extracted from the collected cells by hexane extraction and subjected to dietary oils or fats purification steps (degumming, deoxidation, deodorization, decolorizing) to obtain 150 kg of arachidonic acid-containing triglycerides (triglycerides including a triglyceride wherein all or a portion of the constituent fatty acid is arachidonic acid). The obtained oils or fats (triglycerides) were methylesterified, and the obtained fatty acid methyl ester mixture was analyzed by gas chromatography and found to have an arachidonic acid proportion of 40.64 wt % of the total fatty acid.

The contents of palmitic acid, stearic acid, oleic acid, linoleic acid, γ-linolenic acid and dihomo-γ-linolenic acid were 11.63%, 7.45%, 7.73%, 9.14%, 2.23% and 3.27% by weight, respectively. The arachidonic acid-containing oils or fats (triglycerides) (TGA40S) were also ethylesterified, and the fatty acid ethyl ester mixture including 40 wt % arachidonic acid ethyl ester was separated and purified by an established high-performance liquid chromatography method to obtain 99 wt % arachidonic acid ethyl ester.

Example 2 Production of triglycerides including at least 5 mole percent 8A8

After suspending 100 g of an ion-exchange resin carrier (Dowex MARATHON WBA: Dow Chemical) in 80 ml of *Rhizopus delemar* lipase aqueous solution (12.5% Talipase powder, Tanabe Pharmaceutical Co., Ltd.), 240 ml of cold acetone (−80° C.) was stirred therewith and the mixture was dried under reduced pressure to obtain the immobilized lipase.

Next, 80 g of the triglycerides containing 40 wt % arachidonic acid (TGA40S) obtained in Example 1, 160 g of caprylic acid, 12 g of the aforementioned immobilized lipase and 4.8 ml of water were reacted for 48 hours at 30° C. while stirring (130 rpm). Upon completion of the reaction, the reaction solution was removed to obtain the activated immobilized enzyme.

A 10 g portion of immobilized lipase (*Rhizopus delemar* lipase, carrier: Dowex MARATHON WBA) was than packed into a jacketed glass column (1.8×12.5 cm, 31.8 ml volume), and the reaction oils or fats comprising a mixture of the TGA40S obtained in Example 1 and caprylic acid (TGA40S: caprylic acid=1:2) was flowed through the column at a fixed speed (4 ml/h) for continuous reaction, to obtain 400 g of reaction oils or fats. The column temperature was 40-41° C. The unreacted caprylic acid and free fatty acids were removed from the obtained reaction oils or fats by molecular distillation, and then subjected to dietary oils or fats purification steps (degumming, deoxidation, deodorization, decolorizing) obtain 8A8-containing oils or fats (triglycerides).

The 8A8 proportion of the obtained 8A8-containing oils or fats (triglycerides) was determined by gas chromatography and high-performance liquid chromatography to be 31.6 mole percent. (Incidentally, the proportions of 8P8, 8O8, 8L8, 8G8 and 8D8 were 0.6, 7.9, 15.1, 5.2 and 4.8 mole percent, respectively. The fatty acids P, O, L, G and D bonded at the triglyceride 2-position represent palmitic acid, oleic acid, linoleic acid, γ-linolenic acid and dihomo-γ-linolenic acid, respectively, and therefore 8P8 represents 1,3-capryloyl-2-palmitolein-glycerol, 8O8 represents 1,3-capryloyl-2-oleoyl-glycerol, 8L8 represents 1,3-capryloyl-2-linoleoyl-glycerol, 8G8 represents 1,3-capryloyl-2-γ-linolenoyl-glycerol and 8D8 represents 1,3-capryloyl-2-dihomo-γ-linolenoyl-glycerol). Separation and purification from the obtained 8A8-containing oils or fats (triglycerides) by an established high-performance liquid chromatography method yielded 96 mole percent 8A8.

Example 3 Evaluation of Effect on Behavior Disorder of TGA40S by Behavioral Observation Test The experimental groups consisted of 51 two- to three-month-old male ICR mice, divided into a control diet group (27 mice) and a TGA40S-containing diet group (24 mice), with the control diet or TGA40S-containing diet shown in Table 1 being given to each group. Each group was further divided into non-restrained groups (non-restrained control diet group (9), non-restrained arachidonic acid (ARA) diet group (12)) and restrained groups (restrained control diet group (18), restrained ARA diet group (12)). The restraining was accomplished using a wire mesh restraining tube, once for a 6 hour period three weeks after the start of feeding. The control diet or TGA40S-containing diet shown in Table 1 continued to be fed to each group for the remaining experiment period. The TGA40S used for the TGA40S-containing diet was the product obtained in Example 1.

TABLE 1

| | Experimental diet | |
|---|---|---|
| | Control diet | TGA40S-added diet |
| Casein (g/kg) | 200 | 200 |
| DL-methionine | 3 | 3 |
| Corn starch | 150 | 150 |
| Sucrose | 500 | 500 |
| Cellulose powder | 50 | 50 |
| Corn oil | 50 | 45 |
| Mineral AIN-76 | 35 | 35 |
| Vitamin AIN-76 | 10 | 10 |
| Choline bitartrate | 2 | 2 |
| Vitamin E | 0.05 | 0.05 |
| TGA40S | 0 | 5 |

Since the daily ingestion was approximately 5 g per mouse, the daily intake of TGA40S was 25 mg per mouse. Also, since the total fatty acids bonded to the arachidonic acid-containing oils or fats (triglycerides) prepared in Example 1 included 40 wt % arachidonic acid, the daily intake of arachidonic acid was 10 mg per mouse.

The 6-hour restraint with a wire mesh restraining tube was immediately followed by a behavioral observation test. The behavioral observation test was conducted by transferring the mouse into a new cage and then after 30 minutes observing and recording the behavioral indices according to the Irwin neurobehavioral test method (sniffing, circling, rearing, jumping, digging). No difference was observed between the control diet mice and ARA diet mice in the absence of restraint stress. However, the mice of the control diet group which had experienced restraint stress clearly exhibited increased rearing, indicating cautious reaction, and reduced spontaneous movements such as sniffing and circling, compared to the non-restrained mice, whereas the mice given TAG40S (arachidonic acid) recovered to the same level of behavior as the mice without restraint stress (FIGS. 1, 2).

Thus, for the first time it has been clearly demonstrated that administration of TGA40S improves behavioral patterns which have altered as a result of stress, and that arachidonic acid exhibits an improving effect against behavioral disorders.

Example 4 Preparation of Capsules Comprising Arachidonic Acid-Containing Oils or Fats (Triglycerides)

Water was added to 100 parts by weight of gelatin and 35 parts by weight of food additive grade glycerin for dissolution at 50-60° C., to prepare a gelatin coating with a viscosity of 2000 cp. Next, 0.05 wt % of vitamin E oil was combined with the arachidonic acid-containing oils or fats (triglycerides) obtained in Example 1 to prepare filling 1. Vitamin E oil was also combined at 0.05 wt % with oils or fats (triglycerides) containing 32 mole percent of the 8A8 obtained in Example 2 to prepare filling 2. Also, 50 wt % of the arachidonic acid-containing oils or fats (triglycerides) obtained in Example 1 was combined with 50 wt % fish oil (tuna oil the eicosapentaenoic acid and docosahexaenoic acid proportions of the total fatty acids were 5.1% and 26.5%, respectively) and then 0.05 wt % vitamin E oil was added to prepare filling 3.

Also, 80 wt % of arachidonic acid-containing oils or fats (triglycerides) was combined with 20 wt % fish oil (tuna oil: the eicosapentaenoic acid and docosahexaenoic acid proportions of the total fatty acids were 5.1% and 26.5%, respectively) and then 0.05 wt % vitamin E oil was added to prepare filling 4. Separately, 0.05 wt % of vitamin E oil was combined with the 99% arachidonic acid ethyl ester obtained in Example 1 to prepare filling 5. These fillings 1 to 5 were used for production of soft capsules containing 180 mg of filling per capsule, obtained by capsule molding and drying by ordinary methods.

Example 5 Use for Oil Infusion

After combining 400 g of the oils or fats (triglycerides) containing 96 mole percent 8A8 obtained in Example 2, 48 g of purified egg yolk lecithin, 20 g of oleic acid, 100 g of glycerin and 40 ml of 0.1 N caustic soda and dispersing the mixture with a homogenizer, distilled water for injection was added to make 4 liters. This was emulsified with a high-pressure spray emulsifier to prepare a lipid emulsion. The lipid emulsion was dispensed into plastic bags at 200 ml per bag and then subjected to high-pressure steam sterilization treatment at 121° C. for 20 minutes to prepare an oil infusion.

Example 6 Use for Juice

A 2 g portion of β-cyclodextrin was added to 20 ml of 20% aqueous ethanol, and then 100 mg of the arachidonic acid-containing triglycerides obtained in Example 1 (containing 0.05% vitamin E) were added thereto while stirring with a stirrer, and the mixture was incubated for 2 hours at 50° C. After room temperature cooling (approximately 1 hour), stirring was continued while incubating for 10 hours at 4° C. The resulting precipitate was recovered by centrifugal separation and then washed with n-hexane and lyophilized to obtain 1.8 g of a cyclodextrin clathrate compound comprising arachidonic acid-containing triglycerides. A 1 g portion of this powder was uniformly mixed into 10 L of juice to prepare a juice comprising arachidonic acid-containing triglycerides.

The invention claimed is:

1. A method for treating symptoms or diseases associated with stress-induced behavior disorders, which comprises administering an effective amount of a composition to a patient in need thereof, wherein the composition comprises arachidonic acid and/or a compound comprising arachidonic acid as a constituent fatty acid, and wherein the symptoms or diseases associated with stress-induced behavior disorders are an adjustment disorder, an acute stress disorder, and/or a posttraumatic stress disorder.

2. The method of claim 1, wherein said compound comprising arachidonic acid as a constituent fatty acid is an arachidonic acid alcohol ester, or a triglyceride, phospholipid or glycolipid wherein all or a portion of the constituent fatty acid is arachidonic acid.

3. The method of claim 2, wherein the triglyceride in which all or a portion of the constituent fatty acid is arachidonic acid is a triglyceride having medium chain fatty acids bonded at the 1,3-positions and arachidonic acid bonded at the 2-position.

4. The method of claim 3, wherein said medium chain fatty acids are selected from among C6-12 fatty acids.

5. The method of claim 1, wherein the composition comprises triglycerides which include a triglyceride in which all or a portion of the constituent fatty acid is arachidonic acid.

6. The method of claim 5, wherein the arachidonic acid content of said triglycerides which include a triglyceride in which all or a portion of the constituent fatty acid is arachidonic acid, is at least 10wt % of the total fatty acids of the triglycerides.

7. The method of claim 5, wherein said triglycerides which include a triglyceride in which all or a portion of the constituent fatty acid is arachidonic acid, are extracted from a microorganism belonging to the genus *Mortierella, Conidiobolus, Pythium, Phytophthora, Penicillium, Cladosporium, Mucor, Fusarium, Aspergillus, Rhodotorula, Entomophthora, Echinosporangium* or *Saprolegnia*.

8. The method of claim 5, wherein said triglycerides which include a triglyceride in which all or a portion of the constituent fatty acid is arachidonic acid, are triglycerides containing no eicosapentaenoic acid.

9. The method of claim 1, wherein the composition comprises triglycerides of which at least 5 mole percent consists of a triglyceride having medium chain fatty acids bonded at the 1,3-positions and arachidonic acid bonded at the 2-position.

10. The method of claim 9, wherein said medium chain fatty acids are selected from among C6-12 fatty acids.

11. The method of claim 1, wherein said composition is a food composition or pharmaceutical composition.

12. The method of claim 11, wherein said food composition is a common food (food and drink), functional food, nutritional supplement, food for specified health uses, preterm infant formula, term infant formula, infant food, maternal food or geriatric food.

13. The method of claim 1, wherein the composition further comprises docosahexaenoic acid and/or a compound comprising docosahexaenoic acid as a constituent fatty acid.

14. The method of claim 13, wherein said compound comprising docosahexaenoic acid as a constituent fatty acid is a docosahexaenoic acid alcohol ester, or a triglyceride, phospholipid or glycolipid wherein all or a portion of the constituent fatty acid is docosahexaenoic acid.

15. The method according to claim 13, wherein the composition is characterized in that the arachidonic acid/docosahexaenoic acid ratio (by weight) in the combination of said arachidonic acid and docosahexaenoic acid is in the range of 0.1-15.

16. The method of claim 1, wherein the composition does not contain eicosapentaenoic acid, or the composition comprises eicosapentaenoic acid at an amount that does not exceed 1/5 of the arachidonic acid in the composition.

17. The method of claim 5, wherein said composition is a food composition or pharmaceutical composition.

18. The method of claim 9, wherein said composition is a food composition or pharmaceutical composition.

19. The method of claim 5, wherein the composition further comprises docosahexaenoic acid and/or a compound comprising docosahexaenoic acid as a constituent fatty acid.

20. The method of claim 9, wherein the composition further comprises docosahexaenoic acid and/or a compound comprising docosahexaenoic acid as a constituent fatty acid.

21. The method of claim 5, wherein the composition does not contain eicosapentaenoic acid, or the composition comprises eicosapentaenoic acid at an amount that does not exceed 1/5 of the arachidonic acid in the composition.

22. The method of claim 9, wherein the composition does not contain eicosapentaenoic acid, or the composition comprises eicosapentaenoic acid at an amount that does not exceed 1/5 of the arachidonic acid in the composition.

* * * * *